United States Patent [19]
Herrmann et al.

[11] Patent Number: 6,005,151
[45] Date of Patent: *Dec. 21, 1999

[54] PROCESSS FOR PREPARING AROMATIC OLEFINS USING PALLADACYCLE CATALYSIS

[75] Inventors: Wolfgang Anton Herrmann, Freising; Matthias Beller, Idstein; Ahmed Tafesh, Kelkheim, all of Germany

[73] Assignee: Aventis, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/593,619

[22] Filed: Jan. 30, 1996

[30] Foreign Application Priority Data

Feb. 1, 1995 [DE] Germany .................. 195 03 119

[51] Int. Cl.$^6$ .......................... C07C 15/46; C07C 1/207; C07C 2/66; C07C 2/70
[52] U.S. Cl. .................. 585/438; 585/436; 585/457; 585/462; 585/466; 585/509; 585/511; 585/513; 502/155; 502/156
[58] Field of Search ............. 585/436, 438, 585/457, 462, 466, 509, 511, 514

[56] References Cited

U.S. PATENT DOCUMENTS

| 5,225,603 | 7/1993 | Aslam et al. .................. 568/315 |
| 5,559,277 | 9/1996 | Beller et al. .................. 585/457 |
| 5,703,269 | 12/1997 | Herrmann et al. .................. 585/436 |

FOREIGN PATENT DOCUMENTS

| 2152289 | 12/1995 | Canada . |
| 0 725 049 | 1/1996 | European Pat. Off. . |
| 99 21 730 | 6/1994 | Germany . |
| 44 21 753 | 12/1995 | Germany . |
| 195 15 444 | 11/1996 | Germany . |
| 677662 | 7/1987 | Switzerland . |

OTHER PUBLICATIONS

R. Heck, Acc. Chem. Res., vol. 12, pp. 146–151, Dec. 1979.
A. Rheingold et al., Organometallics, vol. 3, pp. 1414–1417, Sep. 1994.
W. Herrmann et al., Angew. Chem. Int. Ed. Engl., vol. 34, No. 17, pp. 1844–1848, 1995.
Quality Update memo, U.S. Patent and Trademark Office, No. 90–1, Feb. 1990.
Journal of Organic Chemistry, vol. 49, No. 9, May 4, 1984, pp. 1640–1646, T. Mitsudo et al: "Palladium–catalyzed syntheses of aryl polyenes".

Primary Examiner—Mark L. Bell
Assistant Examiner—J. Pasterczyk
Attorney, Agent, or Firm—Connolly Bove Lodge & Hutz LLP

[57] ABSTRACT

The invention relates to a process for preparing monofunctional, bifunctional or polyfunctional aromatic olefins of the formula (I)

(I)

wherein a palladium compound of the formula (IV)

(IV)

is used as a catalyst in the preparation of the compounds of the formula (I).

21 Claims, No Drawings

PROCESSS FOR PREPARING AROMATIC OLEFINS USING PALLADACYCLE CATALYSIS

The present invention relates to a new process for preparing aromatic olefins using novel catalysts, so-called palladacycles.

Aromatic olefins have industrial importance as fine chemicals, starting materials for polymers, UV absorbers and precursors of active compounds.

A frequently used method of synthesizing aromatic olefins in universities is the Heck reaction in which iodo- or bromoaromatics and, in exceptional cases, chloroaromatics are reacted with olefins in the presence of palladium catalysts. Overviews describing this methodology are given in, for example, R. F. Heck, Acc. Chem. Res. 1979, 12, 146; R. F. Heck, Org. React. 1982, 27, 345; R. F. Heck, Palladium Reagents in Synthesis, Academic Press, London 1985.

Catalysts used for the purposes of the Heck reaction are palladium compounds. Although both palladium(II) and palladium(0) complexes are used in Heck reactions, it is generally accepted that only palladium(0) compounds are the actual catalysts of the reaction. In particular, there are formulated in the literature as coordinatively unsaturated 14-electron palladium(0) species which are generally stabilized with weak donor ligands such as phosphines.

Despite the numerous publications on the subject of the Heck reaction, no examples of an industrial implementation of the methodology have been known hitherto. This can be attributed to the fact that the catalyst systems described frequently give satisfactory catalytic turnover numbers only with uneconomic starting materials such as iodoaromatics. Otherwise, in the case of bromoaromatics and, in particular, in the case of chloroaromatics, generally large amounts of catalyst, usually 1–5 mol %, have to be added to achieve industrially useful conversions. In addition, owing to the complexity of the reaction mixtures, no simple catalyst recycling is possible, so that the catalyst costs too generally stand in the way of industrial implementation.

There was therefore a great need for a process which does not have the specified disadvantages, is suitable for use in industry and gives aromatic olefins in high yield and purity.

This object is achieved by a process for preparing monofunctional, bifunctional and polyfunctional aromatic olefins of the formula (I)

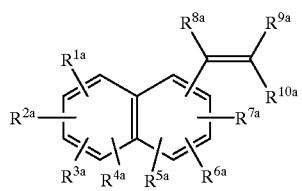

(I)

where $R^{1a}$ to $R^{7a}$ are, independently of one another, hydrogen, $C_1$–$C_8$-alkyl, alkoxy-($C_1$–$C_8$), acyloxy-($C_1$–$C_8$), O-phenyl, phenyl, fluorine, chlorine, bromine, iodine, OH, $NO_2$, $OSO_2CF_3$, CN, COOH, CHO, $SO_3H$, $SO_2R$, SOR, $NH_2$, NH-alkyl-($C_1$–$C_8$), N-alkyl$_2$-($C_1$–$C_8$), $CHal_3$, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NCOO-alkyl-($C_1$–$C_4$), CO-phenyl, COO-phenyl, PO-phenyl$_2$, PO-alkyl$_2$-($C_1$–$C_4$), where one of the radicals $R^{1a}$ to $R^{7a}$ can also be

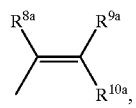

$R^{8a}$ is hydrogen, alkyl-($C_1$–$C_8$), phenyl, O-alkyl-($C_1$–$C_8$), fluorine $R^{9a}$ and $R^{10a}$ are, independently of one another, hydrogen, CN, $CO_2H$, $CO_2$-alkyl-($C_1$–$C_8$), $CONH_2$, CONH-alkyl-($C_1$–$C_4$), CON(alkyl)$_2$-($C_1$–$C_4$), fluorine, $CO_2$-phenyl, alkyl, ($C_1$–$C_8$)-phenyl, PO(phenyl), PO(alkyl-($C_1$–$C_4$))$_2$, CO-phenyl, CO-alkyl-($C_1$–$C_4$), O-alkyl-($C_1$–$C_4$), NH-alkyl-($C_1$–$C_4$), $PO_3H$, $SO_3H$, $SO_3$-alkyl-($C_1$–$C_4$), $SO_2$-alkyl-($C_1$–$C_4$), O-phenyl, CHO, by reaction of haloaromatics of the formula (II)

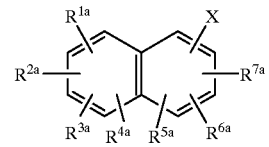

(II)

with olefins of the formula (III)

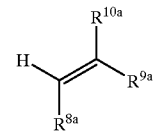

(III)

where $R^{1a}$ to $R^{10a}$ are as defined above, where one of the radicals $R^{1a}$ to $R^{7a}$ can also be X and X is iodine, bromine, chlorine, $OSO_2CF_3$, $OSO_2$phenyl, $OSO_2CH_3$, wherein a palladium compound of the formula (IV)

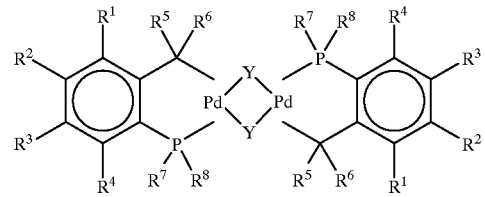

(IV)

where $R^1$, $R^2$, $R^3$, $R^4$, $R^5$, $R^6$ are, independently of one another, hydrogen, ($C_1$–$C_4$)-alkyl, ($C_1$–$C_4$)-alkoxy, fluorine, $NH_2$, NH-alkyl-($C_1$–$C_4$), N-(alkyl)$_2$-($C_1$–$C_4$), $CO_2$alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$, $R^8$ are ($C_1$–$C_8$)-alkyl, ($C_3$–$C_{12}$)-cycloalkyl, substituted or unsubstituted aryl and Y is an anion of an inorganic or organic acid, is used as catalyst.

In many cases, compounds of the formula (IV) in which $R^1$ to $R^6$ are hydrogen, alkyl-($C_1$–$C_4$), phenyl, cycloalkyl-($C_5$–$C_8$), $R^7$ and $R^8$ are phenyl, tolyl, xylyl, mesityl, alkyl ($C_1$–$C_8$) and cycloalkyl($C_5$–$C_8$) and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate or pyrazolyl have been found to be useful.

Well suited compounds are, for example, those in which $R^1$–$R^6$ are H, alkyl, phenyl and $R^7$, $R^8$ are alkyl, phenyl, tolyl, mesityl and xylyl.

Very good results are given by the compounds:
trans-di-$\mu$-acetato-bis[o-(di-o-tolylphosphino)benzyl]dipalladium(II)
trans-di-$\mu$-chloro-bis[o-(di-o-tolylphosphino)benzyl]dipalladium(II)
trans-di-$\mu$-bromo-bis[o-(di-o-tolylphosphino)benzyl]dipalladium(II)
trans-di-$\mu$-iodo-bis[o-(di-o-tolylphosphino)benzyl]dipalladium(II)
trans-di-$\mu$-acetato-bis[o-(dimesitylphosphino)-3,5-dimethylbenzyl]dipalladium(II)
trans-di-$\mu$-chloro-bis[o-(dimesitylphosphino)-3,5-dimethylbenzyl]dipalladium(II)
trans-di-$\mu$-bromo-bis[o-(dimesitylphosphino)-3,5-dimethylbenzyl]dipalladium(II)
trans-di-$\mu$-iodo-bis[o-(dimesitylphosphino)-3,5-dimethylbenzyl]dipalladium(II)
trans-di-$\mu$-acetato-bis[o-(t-butyl-o-tolylphosphino)benzyl]dipalladium(II)
trans-di-$\mu$-acetato-bis[o-(di-t-butylphosphino)benzyl]dipalladium(II)
trans-di-$\mu$-acetato-bis[o-(cyclohexyl-o-tolylphosphino)benzyl]dipalladium(II).

The process has been found to be particularly useful for the preparation of compounds of the formula (I) in which:
$R^{1a}$ to $R^{7a}$ are, independently of one another, hydrogen, ($C_1$–$C_8$)-alkyl, ($C_1$–$C_8$)-alkoxy, ($C_1$–$C_8$)-acyloxy, phenyl, fluorine, chlorine, $NO_2$, CN, COOH, CHO, $SO_2R$, OH, NH-($C_1$–$C_8$)-alkyl, N[($C_1$–$C_8$)alkyl]$_2$, COO-($C_1$–$C_8$)-alkyl, $CONH_2$, CO-($C_1$–$C_8$)-alkyl, CO-phenyl, COO-phenyl, PO-(phenyl)$_2$,
$R^{8a}$ is hydrogen, ($C_1$–$C_8$)-alkyl,
$R^{9a}$, $R^{10a}$ are, independently of one another, hydrogen, CN, $CO_2H$, $CO_2$-($C_1$–$C_8$)-alkyl, $CO_2$-phenyl, ($C_1$–$C_8$)-alkyl, CO-phenyl, CO-($C_1$–$C_4$)-alkyl.

The process is important, for example, for preparing compounds of the formula (I) in which: $R^{1a}$ to $R^{7a}$ are, independently of one another, hydrogen, ($C_1$–$C_8$)-alkyl, ($C_1$–$C_8$)-alkoxy, phenyl, fluorine, chlorine, $NO_2$, CN, COOH, CHO, COO-($C_1$–$C_8$)-alkyl, $CONH_2$, OH, CO-($C_1$–$C_8$)-alkyl, CO-phenyl, PO-(phenyl)$_2$, $R^{8a}$ is hydrogen, $R^{9a}$, $R^{10a}$ are, independently of one another, CN, $CO_2H$, $CO_2$-($C_1$–$C_8$)-alkyl, hydrogen, $CO_2$-phenyl, CO-phenyl, CO-($C_1$–$C_4$)-alkyl.

The process is of particular interest for preparing compounds of the formula (I) in which 4, in particular 5, preferably 6, of the radicals $R^{1a}$ to $R^{7a}$ are hydrogen. Among these, the syntheses of alkyloxyvinylnaphthalenes, hydroxyvinylnaphthalenes, acyloxyvinylnaphthalenes, 4-(hydroxynaphthyl)but-3-en-2-ones, 4-(alkoxynaphthyl)but-3-en-2-ones, 4-(acyloxynaphthyl)but-3-en-2-ones and particularly of 6-methoxy-2-vinylnaphthalene and 4-(6-methoxynaphthyl)but-3-en-2-ones are, in particular, of great industrial importance.

Solvents used are generally inert organic solvents. Well suited solvents are dipolar aprotic solvents such as dialkyl sulfoxides, N,N-dialkylamides of aliphatic carboxylic acids or alkylated lactams. Here, preference is given to dimethyl sulfoxide, dimethylacetamide, dimethylformamide and N-methylpyrrolidone.

The reaction proceeds at temperatures of from 20 to 200° C., in many cases it has been found to be useful to carry out the reaction at temperatures of from 60 to 180° C., preferably from 100 to 150° C.

Since HX is eliminated in the reaction, it is advantageous to neutralize this acid by adding a base. Suitable bases for this purpose are primary, secondary or tertiary amines such as alkylamines, dialkylamines, trialkylamines, which can be alicyclic or open-chain, and alkali metal or alkaline earth metal salts of aliphatic or aromatic carboxylic acids or of carbonic acid, such as lithium, sodium, potassium, calcium, magnesium acetate and corresponding carbonates or hydrogencarbonates.

The palladium catalysts used are generally synthesized separately prior to the actual reaction, but they can also be generated in situ without the initial catalytic activity being reduced thereby. However, if the reaction is relatively prolonged, the in situ mixtures (molar ratio Pd:P=1:1) prove to be not very stable and frequently lead to precipitation of palladium. Therefore, in the case of in situ mixtures, it is necessary to work with an excess of phosphine which is not needed when the palladacycles are used.

The synthesis of the palladium catalysts used is carried out according to the process of the German Patent Application P 44 21 753.

The palladacycles used or formed generally have a dimeric structure. However, in the case of certain compounds (e.g. Y=acetylacetone, hexafluoroacetylacetone), monomeric, oligomeric or even polymeric structures can also be present.

During the catalysis cycle, the dimeric structure is broken up by bridge-cleavage reactions with inorganic and organic nucleophiles so that the actual catalytically active species are to be considered to be the mononuclear complexes of the formula (V) or (VI)

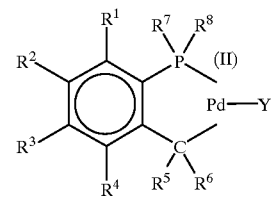

(V)

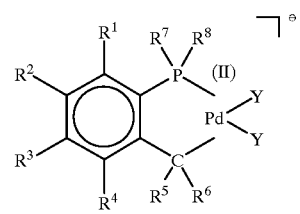

(VI)

The complexes of the formulae (V) and (VI) are in equilibrium with the dimers actually used and have a neutral or anionic character. The mononuclear complex of the formula (V) may here contain further donor ligands on the palladium atom.

The very advantageous course of the reaction of the present invention was particularly surprising since according to the prior art palladium catalysts of the formula (IV) were considered unsuitable for carrying out the Heck reaction.

Thus, R. F. Heck expressly states that palladacycles possess no catalytic activity for the arylation of olefins (T. Mitsudo, W. Fischetti, R. F. Heck, J. Org. Chem., 1984, Vol. 49, 1640).

A. L. Rheingold and W. C. Fultz too (Organometallics, 1984, Vol. 3, 1414) say that the Heck reaction of iodoaromatics with dienes in the presence of palladium acetate and tris(o-tolyl)phosphine results in formation of palladacycles which have no catalytic activity.

In view of this background, the advantages of the catalysts used in the process of the invention are most unexpected and particularly surprising.

The palladacycles used as novel catalyst systems are notable for a very high activity combined, unexpectedly, with high stability.

The stability of the palladacycles in solution can be increased by addition of alkali metal salts, alkaline earth metal salts and transition metal salts of transition groups 6 to 8. In particular, the addition of halides and pseudohalides (e.g. $CN^-$) effects, in the reaction of chloroaromatics, significant yield increases (from 1 to 100%) and improvements in the operating life of the homogeneous catalyst. Suitable salts also include trialkylaimonium and tetraalkylanmmonium salts and corresponding phosphonium and arsonium salts.

Turnover numbers in the order of 100,000 and more can thus be realized.

Owing to the catalyst activities and stability, it is thus possible, for certain processes, to use extremely small amounts of catalyst, so that the catalyst costs are, in comparison with conventional Heck reactions, not cost-limiting for the corresponding process.

Furthermore, the use of very minimal amounts of catalyst gives ecological advantages, since waste products or work-up processes associated with waste products are avoided.

The following examples serve to illustrate the process of the present invention, without restricting it to them.

EXAMPLE 1

Synthesis of the Catalyst

1. Trans-di($\mu$-acetato-bis[o-(di-o-tolylphosphino)benzyl]dipalladium(II) (1)

4.5 g (20 mmol) of $Pd(OAc)_2$ are dissolved in 500 ml of toluene, giving a reddish brown coloration. This solution is admixed with 8.0 g (26.3 mmol) of tri(o-tolyl)phosphine. The solution, which rapidly becomes clear and light orange in color, is heated for 3 minutes at barely 50° C. and then cooled to room temperature. The solvent is removed under reduced pressure to ¼ of the volume. After addition of 500 ml of hexane, the precipitate formed is filtered off. This gives 8.8 g (93% of theory), based on $Pd(OAc)_2$ of (1) as a yellow solid (mp. >200° C.). (1) can be isolated in analytically pure form as yellow crystalline needles by recrystallization from toluene/hexane or methylene chloride/hexane and filtration of the solutions through Celite®.

Elemental analysis: found: C, 58.89%; H, 5.06%; P, 6.92%; O, 6.47%; Pd, 21.84%; $C_{46}H_{46}O_4P_2Pd_2$ (937.62) calc.: C, 58.93%; H, 4.94%; P, 6.61%; O, 6.83%; Pd, 22.70%;

IR ($cm^{-1}$, KBr): 3052m, 3007m, 2954w, 2925m $\nu$(CH); 1578vs $\nu(\mu_2$-C=O), 1468s; 1630 $\nu$(C=C); 1578, 1416 $\nu(\mu_2$-CO); 1341;

$^1$H-NMR (400 MHz, −70° C., $CD_2Cl_2$): δ=7.31 (4H, m, $H_{tolyl}$); 7.21 (2H, m, $H_{tolyl}$); 7.12 (6H, m, $H_{tolyl}$); 7.06 (2H, t, $H_{benzyl}$), $^3$J(HH)=7.3 Hz); 6.92 (4H, m, $H_{tolyl}$); 6.70 (2H, t, $H_{benzyl}$, $^3$J(HH)=7.3 Hz); 6.56 (2H, t, $H_{benzyl}$, $^3$J(HH)=9 Hz); 6.35 (2H, dd, $H_{benzyl}$, $^3$J(HH)=7.9 Hz, $^4$J(PH)=12.2 Hz); 3.00 (6H, s, $CH_3$); 2.81 (2H, dd, $CH_aH_b$, $^2$J($H_aH_b$)= 14.0 Hz, $^3$J(PH)=4.3 Hz); 2.40 (2H, dd, $CH_1H_b$, $^2$J($H_aH_b$)= 14.0 Hz, $^3$J(PH)=1.8 Hz); 2.10 (6H, s, $CH_3$); 1.91 (s, 6H, $CH_3$); $^{13}C\{^1H\}$-NMR (100.5 MHz, −70° C., $CD_2Cl_2$): δ=178.5 (s, $CH_3CO_2$); 157.1 (d, $C_{Ar}$, J(PC)=31.3 Hz); 141.1 (d, $C_{Ar}$, J(PC)=16.0 Hz); 141.0 (d, $C_{Ar}$, J(PC)=21.0 Hz); 133.0 (s, $C_{Ar}$); 132.5 (d, $C_{Ar}$, J(PC)=4.6 Hz); 132.4 (d, $C_{Ar}$, J(PC)=6.1 Hz); 131.7 (d, $C_{Ar}$, J(PC)=8.8 Hz); 131.4 (d, $C_{Ar}$; J(PC)=13.7); 131.3 (d, $C_{Ar}$, J(PC)=9.9 Hz); 130.4 (d, $C_{Ar}$, J(PC)=16.0 Hz); 129.9 (s, $C_{Ar}$); 129.1 (d, $C_{Ar}$, J(PC)=46.2 Hz); 128.7 (s, $C_{Ar}$); 128.1 (d, $C_{Ar}$, J(PC)=33.2 Hz); 127.6 (d, $C_{Ar}$, J(PC)=23.7 Hz); 125.6 (d, $C_{Ar}$, J(PC)=7.3 Hz); 125.2 (d, $C_{Ar}$, J(PC)=7.3 Hz); 124.9 (d, $C_{Ar}$, J(PC)=11.4 Hz); 30.8 (s, $CH_2$); 24.7 (d, $\underline{C}H_3CO_2$, 4J(PC)=3.1 Hz); 23.0 (d, $CH_3$, 3J(PC)=13.7 Hz); 22.2 (d, $CH_3$, 3J(PC)=6.9 Hz);

$^{31}P\{^1H\}$-NMR (161.9 MHz, −70° C., $CD_2Cl_2$): δ=34.2 (s);

Cl-MS (150 eV): m/z=939 [$M^+$+H], 880 [$M^+$-OAc], 819 [$M^+$-2OAc], 714 [$Pd\{o-CH_2C_6H_4P(o-tol)_2\}_2^+$].

EXAMPLE 2

Preparation of 2-vinyl-6-methoxynaphthalene 23.7 g of 2-bromo-6-methoxynaphthalene (100 mmol) are dissolved in 150 ml of N,N-dimethylacetamide. 1 mg of 2,6-di-tert-butylphenol, 10 g of NaOAc (1.2 eq) and 50 mg of palladacycle are added. The solution is transferred to a V4A stirred autoclave and is stirred at 140° C. under an ethylene pressure of 20 bar until conversion is complete. Time: from 10 to 16 hours Conversion: >95% (GC)

Yield: 89%

Work-up: After cooling to RT, the solid is filtered off and washed with 20 ml of DMAc. The product is precipitated from the mother liquor using 200 to 400 ml of 5% HCl. The solution is to be held at room temperature during the HCl addition. The precipitated solid is washed in portions with MeOH and is dried under high vacuum.

EXAMPLE 3

Preparation of 2-vinyl-6-methoxynaphthalene

The procedure is similar to that of Example 2.

Pressure: 30 bar of ethylene

Conversion: 87%

Yield: 80%

EXAMPLE 4

Preparation of 4-(6-methoxynaphthyl)but-3-en-2-one

Reaction under protective gas 6.0 g of 2-bromo-6-methoxynaphthalene (25.3 mmol) are dissolved in 25 ml of N,N-dimethylacetamide. 1 mg of 2,6-di-tert-butylphenol, 3.2 g of NaOAc (1.2 eq) and 1.2 mg of palladacycle (0.01 mol %) are added. After the addition of 3.1 ml of methyl vinyl ketone (1.5 eq), the mixture is stirred for from 6 to 8 hours at 140° C. Conversion: 100% (GC)

Work-up: After cooling to RT, the solid is filtered off and washed with from 20 to 40 ml of dichloromethane. The mother liquor is extracted 3 times with 20 ml of water and the organic phase is subsequently evaporated on a rotary evaporator. After column chromatography, a yield of 87% is obtained.

EXAMPLE 5

Preparation of 4-(6-methoxynaphthyl)but-3-en-2-one

Reaction under protective gas

The procedure is similar to that of Example 4. The base used was 1.2 eq of sodium carbonate.

Conversion: 100% (GC)

Work-up as above. The product was recrystallized from MEOH.

Yield obtained: 82%.

We claim:

1. A process for preparing monofunctional, bifunctional or polyfunctional aromatic olefins of the formula (I)

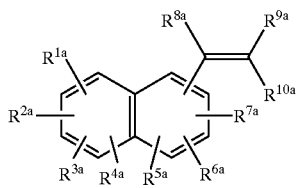
(I)

where $R^{1a}$ to $R^{7a}$ are, independently of one another, hydrogen, $C_1$–$C_8$-alkyl, alkoxy-($C_1$–$C_8$), acyloxy-($C_1$–$C_8$), O-phenyl, phenyl, fluorine, chlorine, bromine, iodine, OH, $NO_2$, $OSO_2CF_3$, CN, COOH, CHO, $SO_3H$, $NH_2$, NH-alkyl-($C_1$–$C_8$), N-alkyl$_2$-($C_1$–$C_8$), NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NCOO-alkyl-($C_1$–$C_4$), CO-phenyl, COO-phenyl, PO-phenyl$_2$, or PO-alkyl$_2$-($C_1$–$C_4$), where one of the radicals $R^{1a}$ to $R^{7a}$ can also be

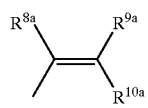

$R^{8a}$ is hydrogen, alkyl-($C_1$–$C_8$), phenyl, O-alkyl-($C_1$–$C_8$), or fluorine $R^{9a}$ and $R^{10a}$ are, independently of one another, hydrogen, CN, $CO_2H$, $CO_2$-alkyl-($C_1$–$C_8$), $CONH_2$, CONH-alkyl-($C_1$–$C_4$), CON(alkyl)$_2$-($C_1$–$C_4$), fluorine, $CO_2$-phenyl, alkyl, ($C_1$–$C_8$)phenyl, PO(phenyl), PO(alkyl-($C_1$–$C_4$))$_2$, CO-phenyl, CO-alkyl-($C_1$–$C_4$), O-alkyl-($C_1$–$C_4$), NH-alkyl-($C_1$–$C_4$), $PO_3H$, $SO_3H$, $SO_3$-alkyl-($C_1$–$C_4$), $SO_2$-alkyl-($C_1$–$C_4$), or O-phenyl, by reaction of haloaromatics of the formula (II)

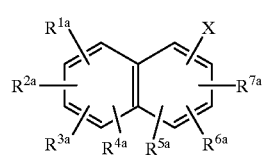
(II)

with olefins of the formula (III)

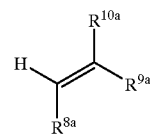
(III)

where $R^{1a}$ to $R^{10a}$ are as defined above, where one of the radicals $R^{1a}$ to $R^{7a}$ can also be X and X is iodine, bromine, chlorine, or $OSO_2CF_3$, in the presence of a dipolar aprotic solvent wherein a palladium compound of the formula (IV)

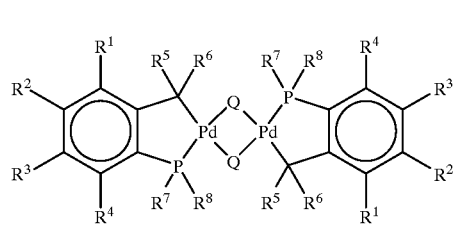
(IV)

where $R^1$, $R^2$, $R^3$, $R^4$, $R^5$, and $R^6$ are, independently of one another, hydrogen, ($C_1$–$C_4$)-alkyl, ($C_1$–$C_4$)-alkoxy, fluorine, $NH_2$, NH-alkyl-($C_1$–$C_4$), N-(alkyl)$_2$-($C_1$–$C_4$), $CO_2$alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$ and $R^8$ are ($C_1$–$C_8$)-alkyl, ($C_3$–$C_{12}$)-cycloalkyl, or substituted or unsubstituted aryl, and Q is an anion of an inorganic or organic acid, is used as a catalyst in the reaction between II and III.

2. The process as claimed in claim 1, wherein, in the formula (IV), $R^1$ to $R^6$ are, independently of one another, hydrogen, ($C_1$–$C_4$)-alkyl, or ($C_5$–$C_8$)-cycloalkyl, $R^7$ and $R^8$ are phenyl, tolyl, xylyl, mesityl, alkyl-($C_1$–$C_8$), or cycloalkyl-($C_5$–$C_8$) and Q is acetate, propionate, benzoate, chloride, bromide, iodide, fluoride, sulfate, hydrogensulfate, nitrate, tetrafluoroborate, tosylate, mesylate, acetylacetonate, hexafluoroacetylacetonate or pyrazolyl.

3. The process as claimed in claim 1, wherein the catalyst used is one of the compounds trans-di-μ-acetato-bis[o-(di-o-tolylphosphino)benzyl]dipalladium(II)

trans-di-μ-chloro-bis[o-(di-o-tolylphosphino)benzyl]dipalladium(II)

trans-di-μ-bromo-bis[o-(di-o-tolylphosphino)benzyl]dipalladium(II)

trans-di-μ-iodo-bis[o-(di-o-tolylphosphino)benzyl]dipalladium(II)

trans-di-μ-acetato-bis[o-(dimesitylphosphino)-3,5-dimethylbenzyl]dipalladium(II)

trans-di-μ-chloro-bis[o-(dimesitylphosphino)-3,5-dimethylbenzyl]dipalladium(II)

trans-di-μ-bromo-bis[o-(dimesitylphosphino)-3,5-dimethylbenzyl]dipalladium(II)

trans-di-μ-iodo-bis[o-(dimesitylphosphino)-3,5-dimethylbenzyl]dipalladium(II)

trans-di-μ-acetato-bis[o-(t-butyl-o-tolylphosphino)benzyl]dipalladium(II)

trans-di-μ-acetato-bis[o-(di-t-butylphosphino)benzyl]
dipalladium(II)

trans-di-μ-acetato-bis[o-(cyclohexyl-o-tolylphosphino)
benzyl]dipalladium(II).

4. The process as claimed in claim 1, wherein, the compound of formula (I) is 6-methoxy-2-vinylnaphthalene or 4-(6-methoxynaphthyl)but-3-en-2-one.

5. The process as claimed in claim 1, wherein in formula (I):

$R^{1a}$ to $R^{7a}$ are, independently of one another, hydrogen, $(C_1-C_8)$-alkyl, $(C_1-C_8)$-alkoxy, $(C_1-C_8)$-acyloxy, phenyl, fluorine, chlorine, $NO_2$, CN, COOH, CHO, NH-$(C_1-C_8)$-alkyl, $N_2$, COO $(C_1-C_8)$-alkyl, $CONH_2$, CO-$(C_1-C_8)$-alkyl, CO-phenyl, COO-phenyl, PO-(phenyl)$_2$, or OH, $R^{8a}$ is hydrogen, or $(C_1-C_8)$-alkyl $R^{8a}$ and $R^{10a}$ are, independently of one another, hydrogen, CN, $CO_2H$, $CO_2$-$(C_1-C_8)$-alkyl, $CO_2$-phenyl, $(C_1-C_8)$-alkyl, CO-phenyl, or CO-$(C_1-C_4)$-alkyl.

6. The process as claimed in claim 1, wherein, in formula (I):

$R^{1a}$ to $R^{7a}$ are, independently of one another, hydrogen, $(C_1-C_8)$-alkyl, $(C_1-C_8)$-alkoxy, phenyl, fluorine, chlorine, $NO_2$, CN, COOH, CHO, COO-$(C_1-C_8)$-alkyl, $CONH_2$, CO-$(C_1-C_8)$-alkyl, CO-phenyl, PO-(phenyl)$_2$, or OH, $R^{8a}$ is hydrogen, $R^{9a}$ and $R^{10a}$ are, independently of one another, CN, $CO_2H$, $CO_2$-$(C_1-C_8)$-alkyl, hydrogen, $CO_2$-phenyl, CO-phenyl, or CO-$(C_1-C_4)$-alkyl.

7. The process is claimed in claim 1, wherein, in formula (I), 4 of the radicals $R^{1a}$ to $R^{7a}$ are hydrogen.

8. The process as claimed in claim 1, wherein, the compound of formula (I) is an alkyloxyvinylnaphthalene, a hydroxyvinylnaphthalene, an acyloxyvinylnaphthalene, a 4-(hydroxynaphthyl)-but-3-en-2-one, a 4-(alkoxynaphthyl) but-3-en-2-one, a 4-(acyloxynaphthyl)but-3-en-2-one.

9. The process as claimed in claim 1, where the dipolar aprotic solvent is a dialkyl sulfoxide, a N,N-dialkylamide, or an alkylated lactam.

10. The process as claimed in claim 9, where the dialkyl sulfoxide is dimethyl sulfoxide, the N,N-dialkylamide is N,N-dimethylacetamide or N,N-dimethylformamide, and the alkylated lactam is N-methyl pyrrolidone.

11. The process as claimed in claim 1, wherein the reaction is carried out at temperatures of from 20 to 200° C.

12. The process as claimed in claim 11, wherein the reaction is carried out at temperatures of from 60° to 180° C.

13. The process as claimed in claim 1
wherein halides of the alkali metals, alkaline earth metals and metals of transition groups 6 to 8 are added.

14. The process as claimed in claim 1,
wherein trialkylammonium or tetraalkylammonium, trialkylphosphonium or tetraalkylphosphonium or trialkylarsonium or tetraalkylarsonium salts are added.

15. The process is claimed in claim 1, wherein, in formula (I), 5 of the radicals $R^{1a}$ to $R^{7a}$ are hydrogen.

16. The process is claimed in claim 1, wherein, in formula (I), 6 of the radicals $R^{1a}$ to $R^{7a}$ are hydrogen.

17. The process as claimed in claim 12, wherein the reaction is carried out at temperatures of from 100 to 150° C.

18. A process for preparing monofunctional, bifunctional or polyfunctional aromatic olefins of the formula (I)

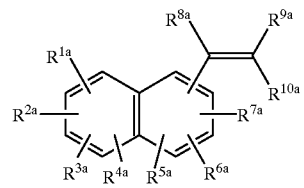

(I)

where $R^{1a}$ to $R^{7a}$ are, independently of one another, hydrogen, $C_1-C_8$-alkyl, alkoxy-$(C_1-C_8)$, acyloxy-$(C_1-C_8)$, O-phenyl, phenyl, fluorine, chlorine, bromine, iodine, OH, $NO_2$, $OSO_2CF_3$, CN, COOH, CHO, $SO_3H$, $NH_2$, NH-alkyl-$(C_1-C_8)$, N-alkyl$_2$-$(C_1-C_8)$, NHCO-alkyl-$(C_1-C_4)$, N-alkyl-$(C_1-C_4)$-CO-alkyl-$(C_1-C_4)$, COO-alkyl-$(C_1-C_8)$, $CONH_2$, CO-alkyl-$(C_1-C_8)$, NHCOH, NCOO-alkyl-$(C_1-C_4)$, CO-phenyl, COO-phenyl, PO-phenyl$_2$, or PO-alkyl$_2$-$(C_1-C_4)$, where one of the radicals $R^{1a}$ to $R^{7a}$ can also be

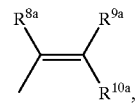

where $R^{8a}$ is hydrogen, alkyl-$(C_1-C_8)$, phenyl, O-alkyl-$(C_1-C_8)$, or fluorine, and $R^{9a}$ and $R^{10a}$ are, independently of one another, hydrogen, CN, $CO_2H$, $CO_2$-alkyl-$(C_1-C_8)$, $CONH_2$, CONH-alkyl-$(C_1-C_4)$, CON(alkyl)$_2$-$(C_1-C_4)$, fluorine, $CO_2$-phenyl, alkyl, $(C_1-C_8)$phenyl, PO(phenyl), PO(alkyl-$(C_1-C_4)$)$_2$, CO-phenyl, CO-alkyl-$(C_1-C_4)$, O-alkyl-$(C_1-C_4)$, NH-alkyl-$(C_1-C_4)$, $PO_3H$, $SO_3H$, $SO_3$-alkyl-$(C_1-C_4)$, $SO_2$-alkyl-$(C_1-C_4)$, or O-phenyl, by reaction of haloaromatics of the formula (II)

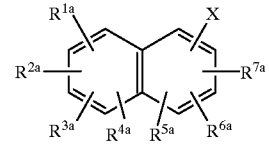

(II)

with olefins of the formula (III)

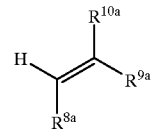

(III)

where $R^{1a}$ to $R^{10a}$ are as defined above, where one of the radicals $R^{1a}$ to $R^{7a}$ can also be X and X is iodine, bromine, chlorine, or $OSO_2CF_3$, in the presence of a dipolar aprotic solvent and at least one of a base and 2,6-di-tert-butyl phenol, wherein a palladium compound of the formula (IV)

(IV)

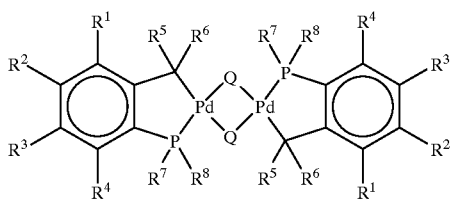

where $R^1$, $R^2$, $R^3$, $R^4$, $R^5$, and $R^6$ are, independently of one another, hydrogen, $(C_1-C_4)$-alkyl, $(C_1-C_4)$-alkoxy, fluorine, $NH_2$, NH-alkyl-$(C_1-C_4)$, N-(alkyl)$_2$-$(C_1-C_4)$, $CO_2$alkyl-$(C_1-C_4)$, OCO-alkyl-$(C_1-C_4)$ or phenyl, or $R^1$ and $R^2$, $R^2$ and $R^3$, $R^3$ and $R^4$, $R^5$ and $R^6$ together form an aliphatic or aromatic ring, and $R^7$ and $R^8$ are $(C_1-C_8)$-alkyl, $(C_3-C_{12})$-cycloalkyl, or substituted or unsubstituted aryl, and Q is an anion of an inorganic or organic acid, is used as a catalyst in the reaction between II and III.

19. The process as claimed in claim 18, wherein the base and 2,6-di-tert-butyl phenol are present.

20. The process as claimed in claim 18, wherein the base is an amine or an alkali metal salt or alkaline earth metal salt of an acid.

21. The process as claimed in claim 20, wherein the amine is an alkylamine, dialkylamine, or trialkylamine, the alkali metal is lithium, sodium, or potassium, the alkaline earth metal is calcium, or magnesium, and the acid is carbonic acid or an aliphatic or aromatic carboxylic acid.

* * * * *

UNITED STATES PATENT AND TRADEMARK OFFICE
CERTIFICATE OF CORRECTION

PATENT NO. : 6,005,151
DATED : December 21, 1999
INVENTOR(S) : Wolfgang Anton Herrmann, Matthias Beller and Ahmed Tafesh It is certified that error appears in the above-identified patent and that said Letters Patent is hereby corrected as shown below:

Claim 5,
Line 10, (column 9, line 18), change "$R^{8a}$" to -- $R^{9a}$ --.

Signed and Sealed this

Eleventh Day of September, 2001

*Attest:*

*Attesting Officer*

NICHOLAS P. GODICI
*Acting Director of the United States Patent and Trademark Office*